US008114882B2

(12) United States Patent
Heinrich et al.

(10) Patent No.: US 8,114,882 B2
(45) Date of Patent: Feb. 14, 2012

(54) (1H-INDOL-7-YL)-(PYRIMIDIN-2-YLAMINO) METHANONE DERIVATIVES AND RELATED COMPOUNDS AS IGF-R1 INHIBITORS FOR THE TREATMENT OF CANCER

(75) Inventors: Timo Heinrich, Gross-Umstadt (DE); Andree Blaukat, Muehltal (DE); Maria Kordowicz, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 1159 days.

(21) Appl. No.: 11/911,268

(22) PCT Filed: Mar. 17, 2006

(86) PCT No.: PCT/EP2006/002470
§ 371 (c)(1),
(2), (4) Date: Oct. 11, 2007

(87) PCT Pub. No.: WO2006/108487
PCT Pub. Date: Oct. 19, 2006

(65) Prior Publication Data
US 2008/0194605 A1 Aug. 14, 2008

(30) Foreign Application Priority Data
Apr. 12, 2005 (DE) .......................... 10 2005 016 634

(51) Int. Cl.
C07D 401/14 (2006.01)
C07D 403/14 (2006.01)
A61K 31/506 (2006.01)

(52) U.S. Cl. ......... 514/256; 514/275; 544/324; 544/328

(58) Field of Classification Search .................. 544/324, 544/328; 514/275, 256
See application file for complete search history.

(56) References Cited

U.S. PATENT DOCUMENTS

| 3,833,658 A | | 9/1974 | Avar et al. | |
|---|---|---|---|---|
| 4,214,086 A | | 7/1980 | Fah | |
| 6,136,837 A | * | 10/2000 | Kai et al. ....................... | 514/400 |
| 6,319,922 B1 | * | 11/2001 | Alexander et al. ............ | 514/241 |
| 2001/0049373 A1 | * | 12/2001 | Chalquest .................... | 514/269 |

FOREIGN PATENT DOCUMENTS

| DE | 21 42 353 A1 | | 3/1972 |
|---|---|---|---|
| DE | 28 47 662 A1 | | 5/1979 |
| JP | 61-236766 | * | 10/1986 |
| WO | WO 03/018021 A | | 3/2003 |
| WO | WO 03/026664 | * | 4/2003 |

OTHER PUBLICATIONS

Simone, Oncology: Introduction, Cecil Textbook of Medicine, 20th Edition, vol. 1, pp. 1004-1010, 1996.*
Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*
Banker et al., Prodrugs, Modern Pharmaceutics, Third Edition, Revised and Expanded, pp. 451 and 596.*
Vippagunta et al., Crystalline Solids, Advanced Drug Delivery Reviews, 48, pp. 3-26, 2001.*
Kobayashi, Pyrimidine-fused 1,4-benzodiazepines. Reaction of 1,4-benzodiazepines with formamide-phosphoryl chloride, Bulletin of the Chemical Society of Japan (1975), 48(11), pp. 302-306.*
West, Solid Solutions, Solid State Chemistry and its applications, pp. 358 & 365, 1988.*
Ulrich, Chapter 4: Crystal Characteristics, Kirk Othmer Encyclopedia of Chemical Technology (7 pages), Aug. 2002.*
LeRoith et al., The insulin-like growth factor system and cancer, Cancer Letters, 195, pp. 127-137 (2003).*
Holt et al., "Benzophenone- and Indolecarboxylic Acids: Potent Type-2 Specific Inhibitors of Human Steroid 5.alpha.-Reductase," Journal of Medicinal Chemistry, vol. 38 No. 1, 1995, pp. 13-15, XP002384662.
Cinque et al., "Structure-Activity Relationship of New Growth Inhibitors of *Trypanosoma cruzi*," Journal of Medicinal Chemistry, vol. 41 No. 9, 1998, pp. 1540-1554, XP002384663.
Sarmiento et al., "Structure-Based Discovery of Small Molecule Inhibitors Targeted to Protein Tyrosine Phosphatase 1B," Journal of Medicinal Chemistry, vol. 43 No. 2, 2000, pp. 146-155, XP002384664.

* cited by examiner

*Primary Examiner* — Deepak Rao
(74) *Attorney, Agent, or Firm* — Millen, White, Zelano & Branigan, P.C.

(57) ABSTRACT

The invention relates to compounds of the formula (I), in which Ar denotes a mono- or bicyclic aromatic homo- or heterocycle having 1 to 4 N, O and/or S atoms and 5 to 10 skeleton atoms, which may be unsubstituted or mono-, di- or trisubstituted by carbonyl oxygen, Hal, A, OH, OA, $NH_2$, NHA, $NA_2$, $NO_2$, CN, OCN, SCN, COOH, COOA, $CONH_2$, CONHA, $CONA_2$, NHCOA, $NHCONH_2$, $NHSO_2A$, CHO, COA, $SO_2NH_2$ and/or $S(O)_9A$, A denotes unbranched, branched or cyclic alkyl having 1-14 C atoms, in which one or two $CH_2$ groups may be replaced by O or S atoms and/or by —CH=CH— groups and/or in addition 1-7 H atoms may be replaced by F and/or Cl, Hal: F, Cl, Br or I, D: NH, $NH_2$, $NA_2$, NHA, $CH_2$, $CH_3$, OH, OA, O or S, E: $CH_2$, CH, NH or N, Y: E or a saturated or unsaturated bond, X: $CH_2$, O or NH, Q: Hal, A, OH, OA, $NH_2$, NHA, $NA_2$, $NO_2$, CN, OCN, SCN, COOH, COOA, $CONH_2$, CONHA, $CONA_2$, NHCOA, $NHCONH_2$, $NHSO_2A$, CHO, COA, $SO_2NH_2$ or X-M, to the preparation and use thereof for the preparation of a medicament for the treatment of diseases, in particular tumors and/or diseases in the development or course of which kinases are involved.

4 Claims, No Drawings

(1H-INDOL-7-YL)-(PYRIMIDIN-2-YLAMINO) METHANONE DERIVATIVES AND RELATED COMPOUNDS AS IGF-R1 INHIBITORS FOR THE TREATMENT OF CANCER

The invention relates to compounds of the formula I

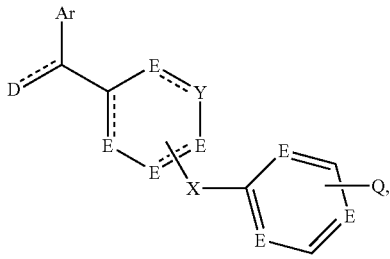

in which
Ar denotes a mono- or bicyclic aromatic homo- or heterocycle having 1 to 4 N, O and/or S atoms and 5 to 10 skeleton atoms, which may be unsubstituted or mono-, di- or trisubstituted by carbonyl oxygen, Hal, A, OH, OA, $NH_2$, NHA, $NA_2$, $NO_2$, CN, OCN, SCN, COOH, COOA, $CONH_2$, CONHA, $CONA_2$, NHCOA, $NHCONH_2$, $NHSO_2A$, CHO, COA, $SO_2NH_2$ and/or $S(O)_gA$,
A denotes unbranched, branched or cyclic alkyl having 1-14 C atoms, in which one or two $CH_2$ groups may be replaced by O or S atoms and/or by —CH=CH— groups and/or in addition 1-7 H atoms may be replaced by F and/or Cl,
Hal denotes F, Cl, Br or I,
D denotes NH, $NH_2$, $NA_2$, NHA, $CH_2$, $CH_3$, OH, OA, O or S,
E denotes $CH_2$, CH, NH or N,
Y denotes E or a saturated or unsaturated bond,
x denotes $CH_2$, O or NH,
Q denotes Hal, A, OH, OA, $NH_2$, NHA, $NA_2$, $NO_2$, ON, OCN, SCN, COOH, COOA, $CONH_2$, CONHA, $CONA_2$, NHCOA, $NHCONH_2$, $NHSO_2A$, CHO, COA, $SO_2NH_2$ or X-M,
M denotes an organic radical consisting of 2 to 40 atoms, at least one atom of which is neither a carbon atom nor a hydrogen atom and
g denotes 0, 1 or 2,
===== denotes a single or double bond,
and pharmaceutically acceptable salts, derivatives, solvates and stereo-isomers thereof, including mixtures thereof in all ratios.

It has been found that the compounds of the formula I are capable of inhibiting, regulating and/or modulating signal transduction mediated by kinases, in particular by tyrosine kinases. In particular, the compounds according to the invention are suitable as inhibitors of tyrosine kinases. Thus, medicaments and pharmaceutical compositions according to the invention can be effectively employed for the treatment of diseases that are caused, mediated and/or propagated by kinases and/or by kinase-mediated signal transduction. Thus, the compounds according to the invention are suitable for the treatment and prophylaxis of cancer, tumour growth, arteriosclerosis, diabetic retinopathy, inflammatory diseases, psoriasis and the like in mammals.

BACKGROUND OF THE INVENTION

Cancer is a disease whose causes are to be seen, inter alia, in disturbed signal transduction. In particular, deregulated signal transduction via tyrosine kinases plays a central role in the growth and spread of cancer (Blume-Jensen, P. and T. Hunter, Nature 411: 355-365, 2001; Hanahan D. and R. A. Weinberg, Cell 100:57-70, 2000). Tyrosine kinases and in particular receptor tyrosine kinases and the growth factors binding to them may thus be involved in deregulated apoptosis, tissue invasion, metastasis and generally in signal transduction mechanisms which lead to cancer.

As already mentioned, one of the principal mechanisms by which cellular regulation is effected is the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is a very widespread process within cells and since cellular phenotypes are largely influenced by the activity of these pathways, it is currently believed that a large number of conditions and/or diseases are attributable to either aberrant activation or functional mutations in the molecular components of kinase cascades. Consequently, considerable attention has been devoted to the characterization of these proteins and compounds that are able to modulate their activity (see review article: Weinstein-Oppenheimer et al., Pharma. &. Therap. 88:229-279, 2000). Various possibilities for the inhibition, regulation and modulation of kinases encompass, for example, the provision of antibodies, antisense ribozymes and inhibitors. In oncology research, tyrosine kinases, in particular, are highly promising targets. Thus, numerous synthetic small molecules are undergoing clinical development as tyrosine kinase inhibitors for the treatment of cancer, for example Iressa® or Gleevec®. However, numerous problems, such as side effects, dosage, resistance of the tumour, tumour specificity and patient selection, still have to be solved here.

Tyrosine kinases are a class of enzymes which catalyse the transfer of the terminal phosphate of adenosine triphosphate to tyrosine residues in protein substrates. It is thought that tyrosine kinases, through substrate phosphorylation, play a crucial role in signal transduction for a number of cellular functions. Although the precise mechanisms of signal transduction are still unclear, tyrosine kinases have been shown to be important factors in cell proliferation, carcinogenesis and cell differentiation.

Tyrosine kinases can be categorised as receptor tyrosine kinases or non-receptor tyrosine kinases. Receptor tyrosine kinases have an extracellular portion, a transmembrane portion and an intracellular portion, while non-receptor tyrosine kinases are exclusively intracellular.

Receptor tyrosine kinases consist of a multiplicity of transmembrane receptors with different biological activity. Thus, about 20 different sub-families of receptor tyrosine kinases have been identified. One tyrosine kinase subfamily, known as the EGFR or HER subfamily, consists of EGFR, HER2, HER3 and HER4. Ligands from this subfamily of receptors include epithelial growth factor (EGF), tissue growth factor (TGF-α), amphiregulin, HB-EGF, betacellulin and heregulin. Another subfamily of these receptor tyrosine kinases is the insulin subfamily, which includes INS-R, IGF-IR and IR-R. The PDGF subfamily includes the PDGF-α and -β receptor, CSFIR, c-kit and FLK-II. In addition, there is the FLK family, which consists of the kinase insert domain receptor (KDR) or VEGFR-2, foetal liver kinase-1 (FLK-1), foetal liver kinase-4 (FLK-4) and fms tyrosine kinase-1 (flt-1) or VEGFR-1. The PDGF and FLK family are usually combined in the group of the split kinase domain receptor tyrosine kinases (Laird, A. D. and J. M. Cherrington, Expert. Opin. Investig. Drugs 12(1): 51-64, 2003) due to the similarities between the two groups. For a detailed discussion of receptor tyrosine kinases, see the paper by Plowman et al., DN & P 7(6):334-339 (1994).

Non-receptor tyrosine kinases likewise consist of a multiplicity of subfamilies, including Src, Frk, Btk, Csk, Abl, Zap70, Fes/Fps, Fak, Jak, Ack, and LIMK. Each of these subfamilies is further sub-divided into different subgroups. For example, the Src subfamily is one of the largest subfamilies. It includes Src, Yes, Fyn, Lyn, Lck, Blk, Hck, Fgr and Yrk. The Src subfamily of enzymes has been linked to oncogenesis. For a more detailed discussion of non-receptor tyrosine kinases, see the paper by Bolen, Oncogene, 8:2025-2031 (1993).

Both receptor tyrosine kinases and non-receptor tyrosine kinases are involved in cellular signal transfer pathways leading to conditions such as cancer, psoriasis and hyperimmune responses.

The present invention relates to compounds of the formula I, preferably as regulators, modulators or inhibitors of receptor tyrosine kinases of the insulin subfamily, which includes the insulin receptor IR, the "insulin like growth factor-1 receptor" IGF-1R and the "insulin related receptor" IRR. The compounds according to the invention are particularly effective in the inhibition of the receptor tyrosine kinase IGF-1R.

As previously mentioned, the insulin-like growth factor-1 receptor (IGF-1R) belongs to the family of transmembrane tyrosine kinase receptors, such as platelet-derived growth factor receptor, the epidermal growth factor receptor, and the insulin receptor. There are two known ligands for the IGF-1R receptor. They are IGF-1 and IGF-2. As used herein, the term "IGF" refers to both IGF-1 and IGF-2. A review of the insulin-like growth factor family of ligands, receptors and binding proteins is given in Krywicki and Yee, Breast Cancer Research and Treatment, 22:7-19, 1992.

IGF/IGF-1R-induced diseases are characterised by an anomalous activity or hyperactivity of IGF/IGF-1R. Anomalous IGF activity refers to either: (1) IGF or IGF-1R expression in cells which do not normally express IGF or IGF-1R; (2) increased IGF or IGF-1R expression leading to undesired cell proliferation, such as cancer; (3) increased IGF or IGF-1R activity leading to undesired cell proliferation, such as cancer, and/or hyperactivity of IGF or IGF-1R. Hyperactivity of IGF or IGF-1R refers to either an amplification of the gene encoding IGF-1, IGF-2, IGF1R or the production of a level of IGF activity which can be correlated with a cell proliferative disease (i.e. as the level of IGF increases, the severity of one or more symptoms of the cell proliferative disease increases) the bioavailability of IGF-1 and IGF-2 can also be affected by the presence or absence of a set of IGF binding proteins (IGF-BPs) of which six are known, Hyperactivity of IGF/IGF-1R can also result from downregulation of IGF-2 which contains an IGF-2 binding domain, but no intracellular kinase domain. Examples of IGF/IGF-1R-induced diseases include the various IGF/IGF-1R-related human malignancies reviewed in Cullen et al., Cancer Investigation, 9(4):443-454, 1991. For the clinical importance and role of IGF/IGF-1Rs in regulating osteoblast function, see Schmid, Journal of Internal Medicine, 234:535-542, 1993.

The activites of IGF-1R thus include: (1) phosphorylation of IGF-1R protein; (2) phosphorylation of an IGF-1R protein substrate; (3) interaction with an IGF adapter protein; (4) IGF-1R protein surface expression. Further IGF-1R protein activities can be identified using standard techniques. IGF-1R activity can be assayed by measuring one or more of the following activities: (1) phosphorylation of IGF-1R; (2) phosphorylation of an IGF-1R substrate; (3) activation of an IGF1R adapter molecule and (4) activation of downstream signalling molecules and/or (5) increased cell division. These activities can be measured using techniques described below and known in the prior art.

IGF-1R has been regarded as essential for the establishment and maintenance of the transformed phenotype in vitro and in vivo in a number of cell types (R. Baserga, Cancer Research 55:249-252, 1995). Herbimycin A has been said to inhibit IGF-1R protein tyrosine kinase and cell proliferation in human breast cancer cells (Sepp-Lorenzino et al., J. Cell Biochem. Suppl. 18b:246, 1994). Experiments studying the role of IGF-1R in transformation that have used antisense strategies, dominant negative mutations, and antibodies to IGF-1R have led to the hypothesis that IGR-1R may be a preferred target for therapeutic interventions.

In addition to its role in nutritional support and in type-II diabetes, IGF-1R has also been associated with several types of cancer. For example, IGF-1 has been implicated as an autocrine growth stimulator for several tumour types, e.g. human breast cancer carcinoma cells (Arteago et al., J. Clin. Invest., 84:1418-1423, 1989) and small lung tumour cells (Macauley et al., Cancer Res., 50:2511-2517, 1989). In addition, IGF-1, while integrally involved in the normal growth and differentiation of the nervous system, also appears to be an autocrine stimulator of human gliomas. Sandberg-Nordqvist et al., Cancer Res., 53:2475-2478 (1993).

An example of the potential involvement of IGF-2 in colorectal cancer may be found in the upregulation of IGF-2 mRNA in colon tumours relative to normal colon tissues (Zhang et al., Science:276; 1268-1272, 1997) IGF-2 may also play a role in hypoxia-induced neovascularisation of tumours. (Mines et al., Int. J. Mol. Med. 5:253-259, 2000) IGF-2 may also play a role in tumourigenesis through activation of an insulin receptor isoform A. IGF-2 activation of insulin receptor isoform A activates cell survival signalling pathways, but its relative contribution to tumour cell growth and survival is unknown at this time. The kinase domain of insulin receptor isoform A is identical to that of the standard insulin receptor (Scalia et al., J. Cell Biochem. 82:610-618, 2001).

The importance of IGF-1R and its ligands in cell types in culture (fibro-blasts, epithelial cells, smooth muscle cells, T-lymphocytes, myeloid cells, chondrocytes and osteoblasts (the stem cells of the bone marrow)) is illustrated by the ability of IGF-1 to stimulate cell growth and proliferation (Goldring and Goldring, Eukaryotic Gene Expression, 1:301-326, 1991). In a series of recent publications, Baserga et al. suggest that IGF-1R plays a central role in the mechanism of transformation and, as such, could be a preferred target for therapeutic interventions in a broad range of human malignant diseases (Baserga, Cancer Res., 55:249-252, 1995; Baserga, Cell, 79:927-930, 1994; Coppola et al., Mol. Cell. Biol., 14:4588-4595, 1994; Baserga, Trends in Biotechnology, 14:150-152, 1996; H. M. Khandwala et al., Endocrine Reviews, 21:215-244, 2000).

The most important types of cancer that can be treated using a compound according to the invention include breast cancer, prostate cancer, colorectal cancer, small-cell lung cancer, non-small-cell lung cancer, multiple myeloma and renal cell carcinoma and endometrial carcinoma.

IGF-1 has also been associated with retinal neovascularisation. Proliferative diabetic retinopathy has been observed in some patients having high levels of IGF-1. (L. E. Smith et al., Nature Medicine, 5:1390-1395, 1999)

However, the compounds according to the invention may also be suitable as anti-ageing agents. It has been observed that there is a link between IGF signalling and ageing. Experiments have shown that calorie-restricted mammals have low levels of insulin and IGF-1 and have a longer life span. Similar observations have also been made in the case of insects (see C. Kenyon, Cell, 105:165-168, 2001; E. Strauss, Science, 292:41-43, 2001; K. D. Kimura et al., Science, 277:942-946, 1997; M. Tatar et al., Science, 292:107-110, 2001).

The present invention thus also relates to the use of the compounds of the formula I for the prevention and/or treatment of diseases in connection with unregulated or disturbed receptor activity. In particular, the compounds according to the invention can therefore be employed in the treatment of certain forms of cancer, such as, for example, breast cancer, prostate cancer, intestinal cancer, small-cell and non-small-cell lung cancer, multiple myeloma, renal-cell carcinoma or corpus carcinoma.

Also conceivable is the use of the compounds according to the invention for the treatment of diabetic retinopathy or for delaying the ageing process. In particular, they are suitable for use in diagnostic methods for diseases in connection with unregulated or disturbed IGF-1R activity.

In addition, the compounds according to the invention can be used to achieve additive or synergistic effects in certain existing cancer chemotherapies and radiotherapies and/or for restoring the efficacy of certain existing cancer chemotherapies and radiotherapies.

A number of aza-heterocyclic compounds have hitherto been described as kinase inhibitors, for example in WO 03/018021, WO 03/018021 or WO 04/056807.

The invention was therefore based on the object of finding novel compounds having advantageous therapeutic properties which can be used for the preparation of medicaments.

Thus, the identification and provision of chemical compounds which specifically inhibit, regulate and/or modulate tyrosine kinase signal transduction is desirable and therefore an aim of the present invention.

DESCRIPTION OF THE INVENTION

It has been found that the compounds of the formula I and salts thereof have very valuable pharmacological properties while being well tolerated. In particular, it has been found that the compounds of the formula I according to the invention surprisingly are effective kinase inhibitors, exhibiting, in particular, a tyrosine kinase-inhibiting action and particularly an IGF-R1-inhibiting action.

In general, all radicals which occur more than once may be identical or different, i.e. are independent of one another. Above and below, the radicals and parameters have the meanings indicated for the formula I unless expressly indicated otherwise.

Accordingly, the invention relates, in particular, to the compounds of the formula I in which at least one of the said radicals has one of the preferred meanings indicated below.

Hal denotes fluorine, chlorine, bromine or iodine, in particular fluorine or chlorine.

A denotes alkyl, is unbranched (linear), branched or cyclic, and has 1, 2, 3, 4, 5, 6, 7, 8, 9, 10, 11, 12, 13 or 14 C atoms.

A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1, 2- or 1,2,2-trimethylpropyl, linear or branched heptyl, octyl, nonyl or decyl.

A very particularly preferably denotes alkyl having 1, 2, 3, 4, 5 or 6 C atoms, in which one or two $CH_2$ groups may be replaced by O or S atoms and/or by —CH=CH— groups and/or in addition 1-7 H atoms may be replaced by F and/or Cl, such as, for example, methyl, ethyl, propyl, isopropyl, butyl, isobutyl, sec-butyl, tert-butyl, pentyl, hexyl, trifluoromethyl, pentafluoroethyl, 1,1-difluoromethyl or 1,1,1-trifluoroethyl.

Cycloalkyl preferably denotes cyclopropyl, cyclobutyl, cylopentyl, cyclohexyl or cycloheptyl. OA is preferably methoxy, furthermore also ethoxy, n-propoxy, isopropoxy, n-butoxy, isobutoxy, sec-butoxy or tert-butoxy.

Ar denotes, for example, unsubstituted phenyl, naphthyl or biphenyl, furthermore preferably, for example, phenyl, naphthyl or biphenyl, each of which is mono-, di- or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methyl-aminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino) phenyl, o-, m- or p-(N,N-dimethylaminocarbonyl)-phenyl, o-, m- or p-(N-ethylamino)phenyl, o-, m- or p-(N,N-diethylamino)-phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4, 6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar furthermore preferably denotes 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2, 3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 2-, 3-, 4- or 5-isoindolyl, 2-, 6, -or 8-purinyl, 1-, 2-, 4- or 5-benzimidazoly, 1-, 3-, 4-, 5-, 6- or 7-benzopyrazoazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 4-, 5-, or 6-phthalazinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl, each of which is unsubstituted or mono-, di- or trisubstituted, for example, by carbonyl oxygen, F, Cl, Br, methyl, ethyl, 1-propyl, 2-propyl, 1-butyl, 2-butyl, t-butyl, phenyl, benzyl, —CH$_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methylsulfonyl.

The heterocyclic radicals may also be partially or fully hydrogenated and also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4-, or -5-pyrrolyl, 1-, 2- or 3-pyrrolidinyl, tetrahydro-1-, -2- or -4-imidazolyl, 2,3-dihydro-1-2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, Tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, 7-, or -8-quinolyl, 1,2,3,4-tetrahydro-1-,-2-,-3-, -4-, -5-, -6-, -7- or -8-isoquinolyl, 2-, 3-, 5-, 6-, 7- or 8- 3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy) phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

The term "substituted" preferably relates to the substitution by the above-mentioned substituents, where a plurality of different degrees of substitution are possible, unless indicated otherwise.

All physiologically acceptable salts, derivatives, solvates and stereoisomers of these compounds, including mixtures thereof in all ratios, are also in accordance with the invention.

The compounds of the formula I may have one or more centres of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrule, for example in the ratio 82:15:3.

An elegant method for the resolution of racemates containing ester groups (for example acetyl esters) is the use of enzymes, in particular esterases.

A preferred group of compounds of the formula I in which Q denotes X-M and X denotes NH conforms to the formula II

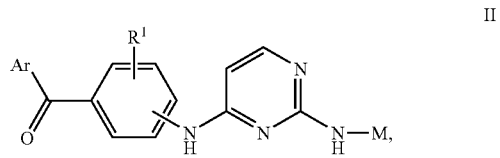

in which Ar, A and M have the meaning indicated for the formula I and

R$^1$ denotes H, Hal, A, OH, OA, NH$_2$, NHA, NA$_2$, NO$_2$, CN, OCN, SCN, COOH, COOA, CONH$_2$, CONHA, CONA$_2$, NHCOA, NHCONH$_2$, NHSO$_2$A, CHO, COA or SO$_2$NH$_2$. In a preferred meaning, R$^1$ is H, Hal, OH, C$_1$-C$_4$-alkyl or CN.

In the compounds of the formula II,

Ar preferably denotes naphthyl, biphenyl, indolyl, isoindolyl, purinyl, quinolinyl, isoquinolinyl, quinoxalinyl, or phthalazinyl, each of which is unsubstituted or substituted as indicated for the formula I, R$^1$ preferably denotes H and M preferably denotes A, A or cycloalkyl, each of which is mono- or polysubstituted by Hal, CN, OCN, SCN, OH or NH$_2$, phenyl, pyridyl, pyrrolyl, pyrazolyl or imidazolyl$_1$ each of which is unsubstituted or mono- or poly-substituted by Hal, A, OH, OA, NH$_2$, NHA, NA$_2$, NO$_2$, CN, COOH, COOA, CONH$_2$, CONHA, CONA$_2$, NHCOA, NHCONH$_2$, NHSO$_2$A, CHO, COA, SO$_2$NH$_2$, phenyl, furyl, phenylcarbonyl, pyrimidylcarbonyl, naphthylcarbonyl, quinolinyl- or isoquinolinylcarbonyl, indolyl- or isoindolylcarbonyl, where M consists of 2 to 40 atoms, at least one atom of which is neither a carbon atom nor a hydrogen atom. M is very particularly preferably quinolinyl or one of the radicals indicated below

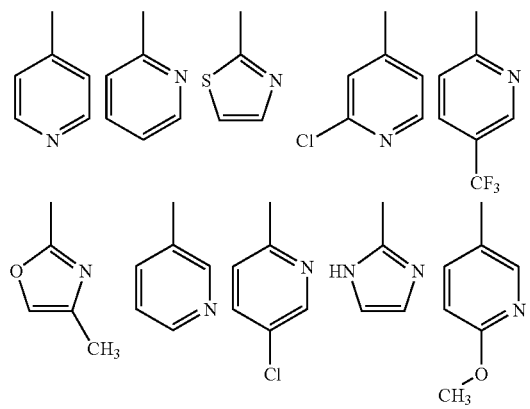

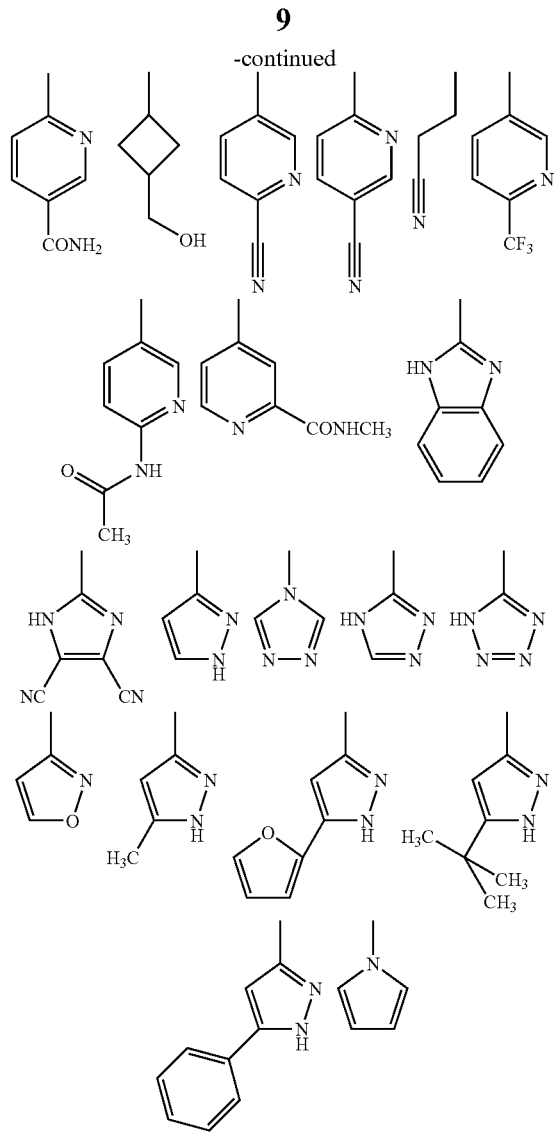

where the linking to the parent structure of the formula II in each case takes place via the bond pointing upwards, which is not a methyl group.

Further preferred sub-groups of compounds of the formula II can be expressed by the following sub-formulae IIa to IId, which conform to the formula II in which
$R^{2'}$, $R^{2''}$ denotes H, Hal, A, OH, OA, $NH_2$, NHA, $NA_2$, $NO_2$, ON, OCN, SCN, COOH, COOA, $CONH_2$, CONHA, $CONA_2$, NHCOA, $NHCONH_2$, $NHSO_2A$, CHO, COA or $SO_2NH_2$ and imidazole, furan, thiophene or oxadiazole and in which the radicals not designated in greater detail have the meaning indicated for the formula II, but in which in the sub-formula IIa

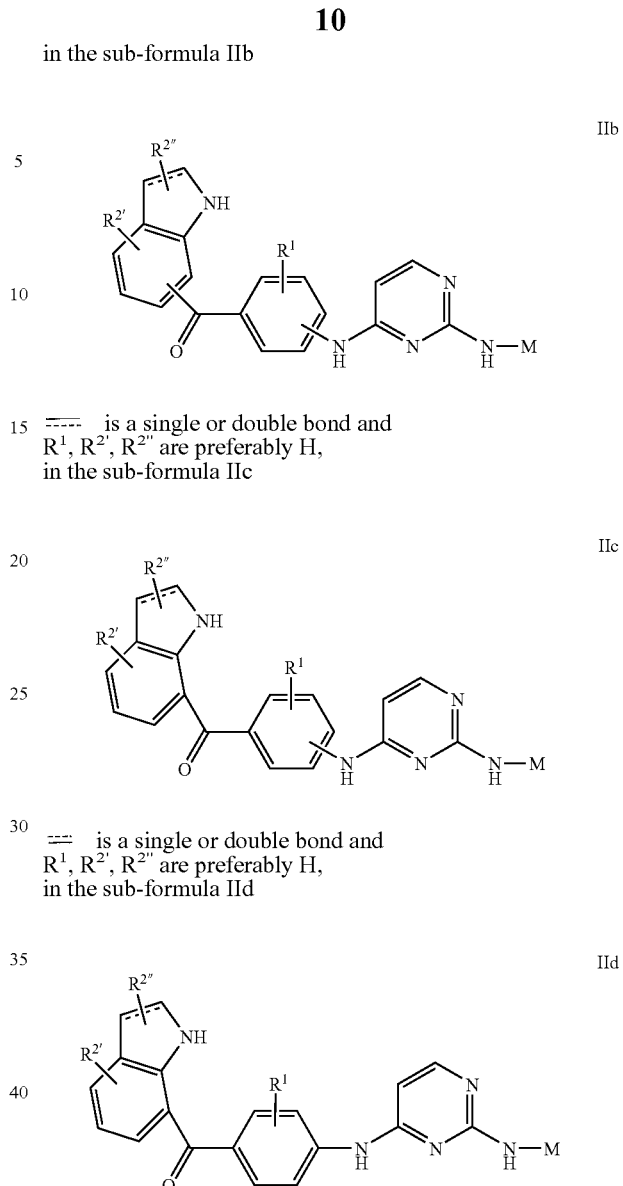

U is N, NH, OS S, or CH,
V is U or is not present,
----- is a single or double bond and
$R^1$, $R^{2'}$, $R^{2''}$ are preferably H,
in the sub-formula IIb ----- is a single or double bond and
$R^1$, $R^{2'}$, $R^{2''}$ are preferably H,
in the sub-formula IIc ----- is a single or double bond and
$R^1$, $R^{2'}$, $R^{2''}$ are preferably H,
in the sub-formula IId ----- is a single or double bond and
$R^1$, $R^{2'}$, $R^{2''}$ are preferably H,
and pharmaceutically acceptable salts, derivatives, solvates and stereo-isomers thereof, including mixtures thereof in all ratios.

A likewise preferred group of compounds of the formula I in which Q denotes Hal, A, OH, OA, $NH_2$, NHA, $NA_2$, $NO_2$, CN, OCN, SCN, COOH, COOA, $CONH_2$, CONHA, $CONA_2$, NHCOA, $NHCONH_2$, $NHSO_2A$, CHO, COA or $SO_2NH_2$ conforms to the formula III

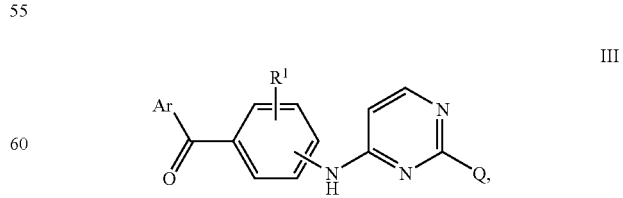

in which Ar, A, M, $R^1$ and $R^{2'}$, $R^{2''}$ have the meaning indicated for the formula II.

Further preferred sub-groups of compounds of the formula III can be expressed by the following sub-formulae IIIa to IIId, which conform to the formula III and in which the radicals not designated in greater detail have the meaning indicated for the formula Ill, in particular the meaning characterised as preferred, but in which
in the sub-formula IIIa

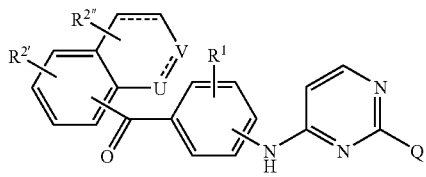

IIIa

U is N, NH, O, S, or CH,
V is U or is not present
----- is a single or double bond,
$R^1$, $R^{2'}$, $R^{2''}$ are preferably H and
Q is preferably Hal,
in the sub-formula IIIb

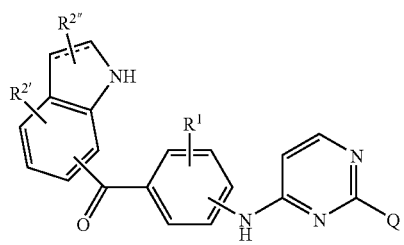

IIIb

----- is a single or double bond,
$R^1$, $R^{2'}$, $R^{2''}$ are preferably H and
Q is preferably Hal, in the sub-formula IIIc

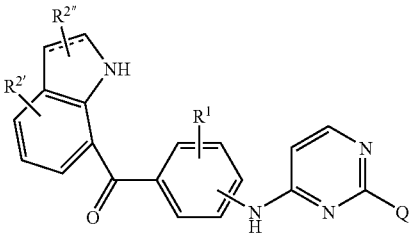

IIIc

----- is a single or double bond,
$R^1$, $R^{2'}$, $R^{2''}$ are preferably H and
Q is preferably Hal,
in the sub-formula IIId

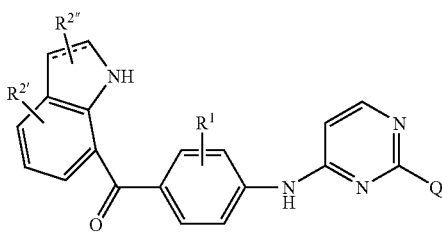

IIId

----- is a single or double bond,
$R^1$, $R^{2'}$, $R^{2''}$ are preferably H and
Q is preferably Hal,
and pharmaceutically acceptable salts, derivatives, solvates and stereo-isomers thereof, including mixtures thereof in all ratios.

Particular preference is given to compounds selected from the compounds listed in Table 1 and pharmaceutically acceptable salts, derivatives, solvates and stereoisomers thereof, including mixtures thereof in all ratios.

TABLE 1

| | IC50 (µM) | Melting point |
|---|---|---|
| (compound 1) | 1.11 | 235-238° C. |
| (compound 2) | 2.6 | 196-197° C. (trifluoroacetate) |

TABLE 1-continued
| | IC50 (μM) | Melting point |
|---|---|---|
| 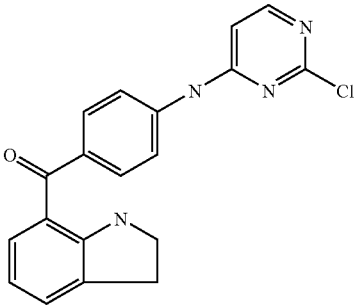 3 | 7.85 | |
| 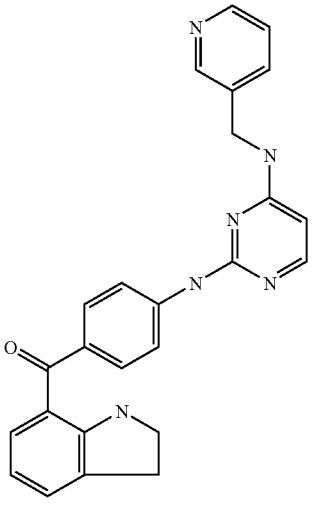 4 | 2.4 | 80-81° C. |
| 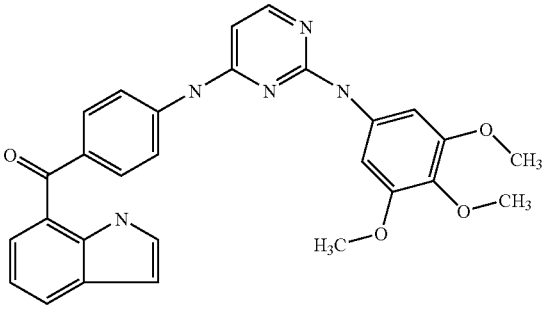 5 | 2.2 | 115-116° C. |
| 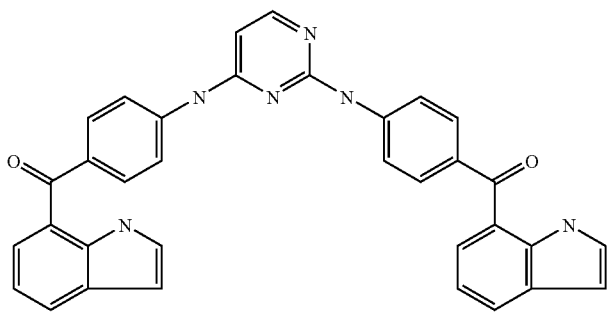 6 | 1.8 | 150° C. decomposition |

TABLE 1-continued
| | IC50 (μM) | Melting point |
|---|---|---|
| 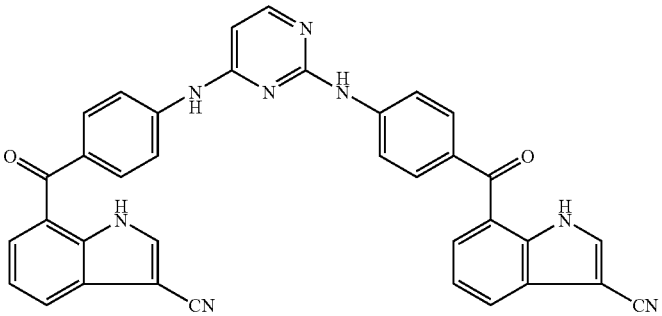 7 | 0.49 | |
| 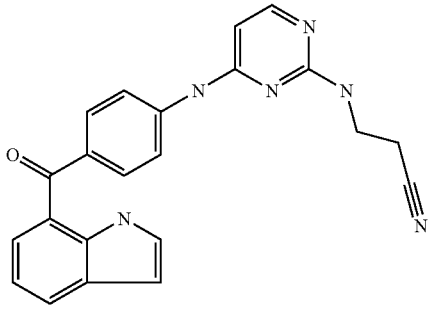 8 | 3.1 | 204-206° C. (hydrochloride) |
| 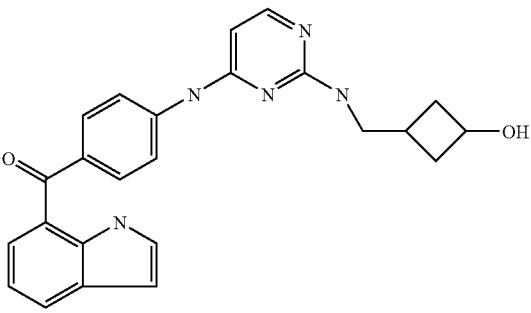 9 | 1.2 | 115-120° C. (hydrochloride) |
| 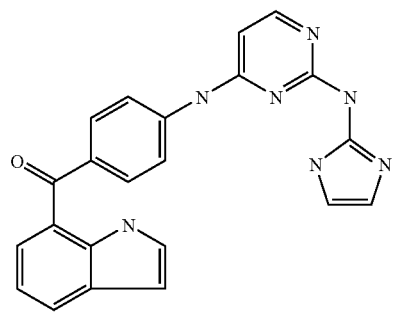 10 | 0.15 | 202-207° C. (hydrochloride) |

TABLE 1-continued
| | IC50 (μM) | Melting point |
|---|---|---|
| 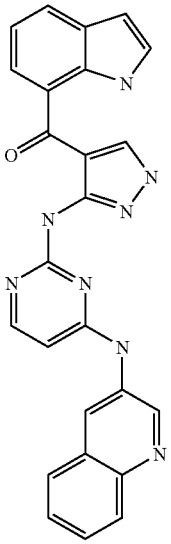  11 | 0.63 | |
| 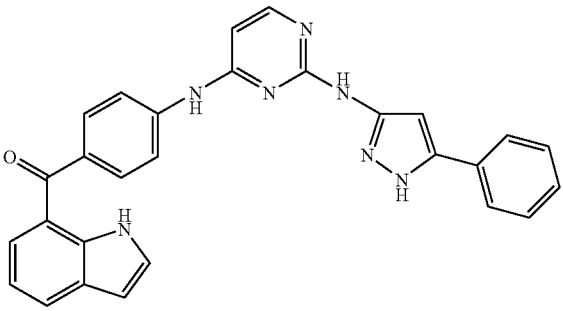  12 | 10 | 166-166.5° C. (trifluoroacetate) |
| 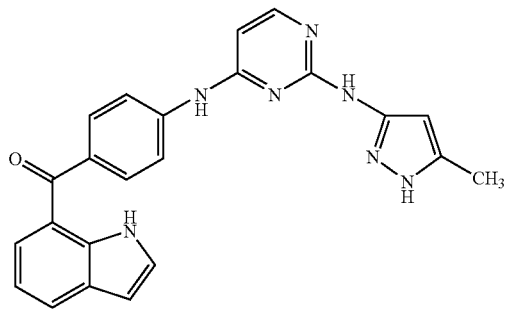  13 | 2.9 | 117-119° C. (trifluoroacetate) |

TABLE 1-continued

| | IC50 (μM) | Melting point |
|---|---|---|
| 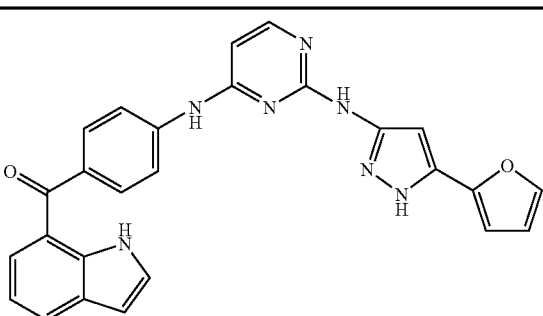<br>14 | 15 | 171-172° C.<br>(trifluoroacetate) |
| 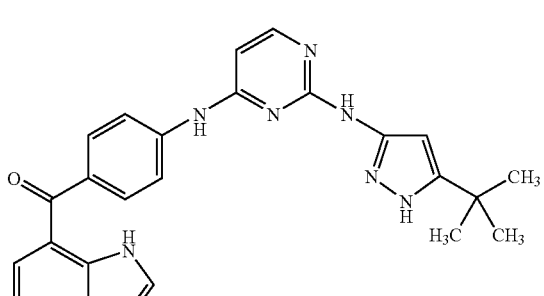<br>15 | 12 | 140-142° C.<br>(trifluoroacetate) |
| 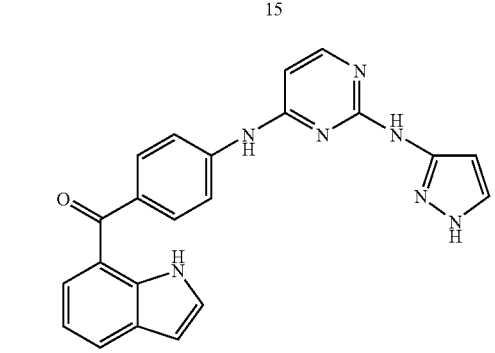<br>16 | 2.4 | 198-200° C.<br>(trifluoroacetate) |

Pharmaceutically or physiologically acceptable derivatives are taken to mean, for example, salts of the compounds according to the invention and also so-called prodrug compounds. Such derivatives are known in the person skilled in the art. A review of physiologically tolerated derivatives is given in Burger's Medicinal Chemistry And Drug Discovery, 5th Edition, Vol 1:Principles and Practice. Prodrug compounds are taken to mean compounds of the formula I which have been modified with, for example, alkyl or acyl groups, sugars or oligopeptides and which are rapidly cleaved or liberated in the organism to give the effective compounds according to the invention. These also include biodegradable polymer derivatives of the compounds according to the invention, as described, for example, in Int. J. Pharm. 115:61-67 (1995).

Suitable acid-addition salts are inorganic or organic salts of all physiologically or pharmacologically acceptable acids, for example halides, in particular hydrochlorides or hydrobromides, lactates, sulfates, citrates, tartrates, maleates, fumarates, oxalates, acetates, phosphates, methylsulfonates or p-toluenesulfonates.

Solvates of the compounds of the formula I are taken to mean adductions of inert solvent molecules onto the compounds of the formula I which form owing to their mutual attractive force. Solvates are, for example, hydrates, such as monohydrates or dihydrates, or alcoholates, i.e. addition compounds with alcohols, such as, for example, with methanol or ethanol.

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or prevention of side effects or also reduction in the progress of a disease, condition or disorder. The term "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The present invention furthermore relates to a process for the preparation of compounds of the formula I and physiologically acceptable salts, derivatives, solvates and stereoisomers thereof, characterised in that a compound of the formula V

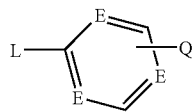

in which E and Q have the above-mentioned meanings and L [lacuna] a leaving group, such as, for example, Cl, Br, I, mesylate, tosylate, phenylsulfonate or trifluoroacetate, is reacted with a compound of the formula IV

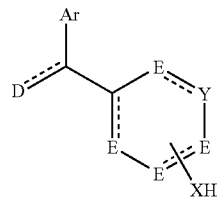

in which E, X, Y, Ar and D have the above-mentioned meanings, and/or a base or acid of the formula I is converted into one of its salts.

The compounds of the formula V and IV are generally known. If they are novel, they can be prepared by methods known per se, as described in the literature (for example in standard works, such as Houben-Weyl, Metho-den der Organischen Chemie [Methods of Organic Chemistry], Georg Thieme Verlag, Stuttgart; Organic Reactions, John Wiley & Sons, Inc., New York).

The compounds of the formula I and also the starting materials for their preparation are prepared by methods known per se, as described in the literature (for example in standard works, such as Houben-Weyl, Metho-den der Organischen Chemie [Methods of Organic Chemistry], Georg Thieme Verlag, Stuttgart; Organic Reactions, John Wiley & Sons, Inc., New York), to be precise under reaction conditions as are known and suitable for the said reactions. Use can also be made here of variants known per se which are not mentioned here in greater detail.

The starting materials for the claimed process can also be formed in situ by not isolating them from the reaction mixture, but instead immediately converting them further into the compounds of the formula I. On the other hand, it is possible to carry out the reaction stepwise.

The aza-heterocyclic compounds of the formula I can preferably be obtained by reacting a starting material of the formula V with a starting material of the formula IV as follows:

A compound of the formula V is dissolved in an inert solvent together with a compound of the formula IV and subsequently stirred at elevated temperature. The reaction mixture is subsequently purified, and the product is isolated as a solid, preferably in crystalline form.

The starting materials of the formulae V and IV are generally known and commercially available; the compounds of the formulae V and IV that are not known can easily be prepared analogously to known compounds. The preparation of the compound of the formula V (2-chloropyrimidin-4-yl)-quinolin-3-ylamine and the compound of the formula IV (4-aminophenyl)-(2,3-dihydro-1H-indol-7-yl)methanone are described in Examples 1 and 2, the preparation of (2,3-dihydro-1H-indol-7-yl)-[4-[4-(quinolin-3-ylamino)-pyrimidin-2-ylamino]phenyl}methanone is described in Example 3.

The reaction described above is generally carried out in an inert solvent. Suitable inert solvents for the reactions described above are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, N-methylpyrrolidone (NMP), dimethylacetamide or dimethylformamide (DMF); nitrites, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Preference is given to sulfoxides, such as dimethyl sulfoxide (DMSO).

The amount of solvent is not crucial, 5 g to 500 g of solvent can preferably be added per g of the compound of the formula I to be formed.

In general, the process is carried out at a pressure of 1 to 200 bar, but preferably at atmospheric pressure.

Depending on the conditions used, the reaction temperature for the reactions described above is between about −10° and 200°, normally between 60° and 180°, preferably between 80° and 120°.

Depending on the conditions used, the reaction time is between a few minutes and a number of days, preferably in the region of a number of hours.

The reaction can also be carried out in the heterogeneous phase, in which case an aqueous phase and a benzene or toluene phase are preferably used. Use is made here of a phase-transfer catalyst, such as, for example, tetrabutylammonium iodide, and optionally an acylation catalyst, such as, for example, dimethylaminopydedine.

A base of the formula I obtained can be converted into the associated acid-addition salt using an acid. Suitable for this reaction are acids which give physiologically acceptable salts. Thus, it is possible to use inorganic acids, for example sulfuric acid, hydrohalic acids, such as hydrochloric acid or hydrobromic acid, phosphoric acids, such as orthophosphoric acid, nitric acid, sulfamic acid, furthermore organic acids, in detail aliphatic, alicyclic, araliphatic, aromatic o r heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenyfpropionic acid, citric acid, gluconic acid, ascorbic acid, nicotinic acid, isonicotinic acid, methane- or ethanesulfonic acid, ethanedisulfonic acid, 2-hydroxyethanesulfonic acid; benzenesulfonic acid, p-toluenesulfonic acid, naphthalenemono- and -disulfonic acids, lauylsulfuric acid.

If desired, the free bases of the formula I can be liberated from their salts by treatment with strong bases, such as sodium hydroxide, potassium hydroxide, sodium carbonate or potassium carbonate, so long as no other acidic groups are present in the molecule.

Compounds of the formula I can furthermore be obtained by liberating them from one of their functional derivatives by treatment with a solvolysing or hydrogenolysing agent.

Preferred starting materials for the solvolysis or hydrogenolysis are those which otherwise conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group and/or those which carry a hydroxyl-protecting group instead of the H atom of a hydroxyl group, for example those which conform to the formula I, but carry a —COOR" group, in which R" denotes a hydroxyl-protecting group, instead of a —COOH group.

Preferred starting materials are also the oxadiazole derivatives, which can be converted into the corresponding amidino compounds.

It is also possible for a plurality of—identical or different—protected amino and/or hydroxyl groups to be present in the molecule of the starting material. If the protecting groups present are different from one another, they can in many cases be cleaved off selectively.

The expression "amino-protecting group" is known in general terms and relates to groups which are suitable for protecting (blocking) an amino group against chemical reactions, but which are easy to remove after the desired chemical reaction has been carried out elsewhere in the molecule, Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1-20, in particular 1-8, C atoms. The expression "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl, butyryl; aralkanoyl, such as phenylacetyl; aroyl, such as benzoyl or tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl), 2-iodoethoxycarbonyl; aralkoxycarbonyl, such as CBZ ("carbobenzoxy", 4-methoxybenzyloxycarbonyl, FMOC; arylsulfonyl, such as Mtr. Preferred amino-protecting groups are BOC and Mtr, furthermore CBZ, Fmoc, benzyl and acetyl.

Furthermore, free amino groups can be acylated in a conventional manner using an acid chloride or anhydride or alkylated using an unsubstituted or substituted alkyl halide, or reacted with CH3-C(=NH)—OEt, advantageously in an inert solvent, such as dichloromethane or THF, and/or in the presence of a base, such as triethylamine or pyridine, at temperatures between −60 and +30°.

The expression "hydroxyl-protecting group" is likewise known in general terms and relates to groups which are suitable for protecting a hydroxyl group against chemical reactions, but which are easy to remove after the desired chemical reaction has been carried out elsewhere in the molecule. Typical of such groups are the above-mentioned unsubstituted or substituted aryl, aralkyl or acyl groups, furthermore also alkyl or silyl groups. The nature and size of the hydroxyl-protecting groups is not crucial since they are removed again after the desired chemical reaction or reaction sequence; preference is given to groups having 1-20, in particular 1-10, C atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I are liberated from their functional derivatives —depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature, RT).

The BOC, OBut and Mtr groups can, for example, preferably be cleaved off using TFA in dichloromethane or using approximately 3 to 5N HCl in dioxane at 15-30° C., the FMOC group can be cleaved off using an approximately 5 to 50% solution of dimethylamine, diethylamine or piperidine in DMF at 15-30° C.

Hydrogenolytically removable protecting groups (for example CBZ, benzyl or the liberation of the amidino group from its oxadiazole derivative) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Esters can be saponified, for example, using acetic acid or using NaOH or KOH in water, water/THF or water/dioxane, at temperatures between 0 and 100°.

Further methods for the removal of protecting groups is described, for example, in Theodora W. Green, Peter G. M. Wuts: Protective Groups in Organic Synthesis, 3rd Edition John Wiley & Sons (1999).

Compounds of the formula I according to the invention may be chiral owing to their molecular structure and accordingly occur in various enantiomeric forms. They can therefore exist in racemic or in optically active form. Since the pharmaceutical activity of the racemates or stereoisomers of the compounds according to the invention may differ, it may be desirable to use the enantiomers. In these cases, the end product or even the intermediates can be separated into enantiomeric compounds by chemical, biochemical or physical measures known to the person skilled in the art or even employed as such in the synthesis.

After removal of the solvent, the compounds of the formula I can be obtained by conventional work-up steps, such as, for example, addition of water to the reaction mixture and extraction. It may be advantageous subsequently to carry out a distillation or crystallisation for further purification of the product.

The invention furthermore relates to medicaments comprising at least one compound according to the invention and/or physiologically acceptable salts, derivatives, solvates and stereoisomers thereof, including mixtures thereof in all ratios.

A pharmaceutical composition according to the invention may furthermore comprise further excipients and/or adjuvants and optionally one or more further medicament active ingredients.

The invention furthermore relates to a process for the preparation of a medicament, characterised in that a compound according to the invention and/or one of its physiologically acceptable salts, derivatives, solvates and stereoisomers, including mixtures thereof in all ratios, is brought into a suitable dosage form together with a solid, liquid or semi-liquid excipient or adjuvant.

The invention also relates to a set (kit) consisting of separate packs of
a) an effective amount of a compound according to the invention and/or physiologically acceptable salts, derivatives, solvates and stereoisomers thereof, including mixtures thereof in all ratios, and
b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Medicaments can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, sex, weight and condition of the patient. Preferred dosage unit formulations are those which comprise a daily dose or part-dose, as indicated above, or a corresponding fraction thereof of an active ingredient. Furthermore, medicaments of this type can be prepared using a process which is generally known in the pharmaceutical art.

Medicaments can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such medicaments can be prepared using all processes known in the pharmaceutical art by, for example, combining the active ingredient with the excipient(s) or adjuvant(s).

Medicaments adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like.

The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil, or natural sweeteners or saccharin or other artificial sweeteners, and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, poly-acetals, polydihydroxypyrans, polycyanoacrylates and crosslinked or amphipathic block copolymers of hydrogels.

Medicaments adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6):318 (1986).

Medicaments adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Medicaments adapted for topical application to the eye include eye drops, in which the active ingredient is dissolved or suspended in a suitable carrier, in particular an aqueous solvent.

Medicaments adapted for topical application in the mouth encompass lozenges, pastilles and mouthwashes.

Medicaments adapted for rectal administration can be administered in the form of suppositories or enemas.

Medicaments adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Medicaments adapted for administration by inhalation encompass finely particulate dusts or mists, which can be generated by various types of pressurised dispensers with aerosols, nebulisers or insufflators.

Medicaments adapted for vaginal administration can be administered as pessaries, tampons, creams, gels, pastes, foams or spray formulations.

Medicaments adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the medicaments according to the invention may also comprise other agents usual in the art with respect to the particular type of pharmaceutical formulation; thus, for example, medicaments which are suitable for oral administration may comprise flavours.

A therapeutically effective amount of a compound of the present invention depends on a number of factors, including, for example, the age and weight of the recipient, the precise condition that requires treatment, and its severity, the nature of the formulation and the method of administration, and is ultimately determined by the treating doctor or vet. However, an effective amount of a compound of the formula I for the treatment of the diseases according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or more usually in a series of part-doses (such as, for example, two, three, four, five or six) per day, so that the total daily dose is the same. An effective amount of a salt or solvate or of a physiologically functional derivative thereof can be determined as a fraction of the effective amount of the compound according to the invention per se.

The compounds according to the invention exhibit an advantageous biological activity which can easily be detected in enzyme assays. In such enzyme-based assays, the compounds according to the invention preferably exhibit and cause an inhibiting effect, which is usually documented by $IC_{50}$ values in a suitable range, preferably in the micromolar range and more preferably in the nanomolar range.

The present invention relates to compounds according to the invention as effectors, preferably as inhibitors of the signalling pathways described herein The invention therefore particularly preferably relates to compounds according to the invention as activators and inhibitors of tyrosine kinases, preferably as inhibitors of receptor tyrosine kinases, in particular from the insulin subfamily, which includes INS-R, IGF-IR and IR-R. The compounds according to the invention are particularly effective here in the inhibition of the receptor tyrosine kinase IGF-1R.

As discussed above, the signalling pathways influenced by the compounds according to the invention are relevant for various diseases. Accordingly, the compounds according to the invention are useful in the prophylaxis and/or treatment of diseases which are dependent on the said signalling pathways through interaction with one or more of the said signalling pathways.

The present invention therefore furthermore relates to the use of compounds according to the invention and/or physiologically acceptable salts, derivatives, solvates and stereoisomers thereof, including mixtures thereof in all ratios, for the preparation of a medicament for the treatment and/or prophylaxis of diseases, in particular diseases that are caused, mediated and/or propagated by kinases and/or by kinase-mediated signal transduction. Preference is given here to tyrosine kinases selected from the group of the receptor tyrosine kinases. Particular preference is given to IGF-1R here.

In addition, the present compounds are suitable as pharmaceutical active ingredients for mammals, in particular for humans, in the treatment of tyrosine kinase-induced diseases. The expression "tyrosine kinase-induced diseases" refers to pathological conditions which are dependent on the activity of one or more tyrosine kinases. Tyrosine kinases participate either directly or indirectly in the signal transduction pathways of a variety of cellular activities, including proliferation, adhesion and migration, as well as differentiation. Diseases associated with tyrosine kinase activity include cancer, tumour growth, arteriosclerosis, diabetic retinopathy and inflammatory diseases.

The diseases discussed here are usually divided into two groups, hyperproliferative and non-hyperproliferative diseases. In this connection, psoriasis, arthritis, inflammation, endometriosis, scarring, benign prostatic hyperplasia, immunological diseases, autoimmune diseases and immunodeficiency diseases are regarded as non-cancerous diseases, of which arthritis, inflammation, immunological diseases, autoimmune diseases and immunodeficiency diseases are usually regarded as non-hyperproliferative diseases.

In this connection, brain cancer, lung cancer, squamous cell cancer, bladder cancer, gastric cancer, pancreatic cancer, hepatic cancer, renal cancer, intestinal cancer, breast cancer, head cancer, neck cancer, oesophageal cancer, gynaecological cancer, thyroid cancer, lymphomas, chronic leukaemia and acute leukaemia are to be regarded as cancerous diseases, all of which are usually counted in the group of hyperproliferative diseases. Especially cancerous cell growth and especially cancerous cell growth mediated directly or indirectly by IGF-1R is a disease which is a target of the present invention.

The present invention therefore relates to the use of compounds according to the invention for the preparation of a medicament for the treatment and/or prophylaxis of the said diseases and also to a method for the treatment of the said diseases which comprises the administration of one or more compounds according to the invention to a patient in need of such an administration.

The recipient or patient can belong to any mammalian species, for example a primate species, particularly humans; rodents, including mice, rats and hamsters; rabbits; horses, cows, dogs, cats, etc. Animal models are of interest for experimental investigations, providing a model for the treatment of human disease.

The responsiveness of a particular cell to treatment with the compounds according to the invention can be determined by in-vitro tests. Typically, a culture of the cell is incubated with a compound according to the invention at various concentrations for a period of time which is sufficient to allow the active ingredients to induce cell death or to inhibit migration, usually between about one hour and one week. In-vitro tests can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the specific cell count, and may be continued until essentially no more undesired cells are detected in the body.

For the identification of kinase inhibitors, various assay systems are available. In scintillation proximity assay (Sorg et al., J. of. Biomolecular Screening:7, 11-19, 2002) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 191-214, 2002).

Other non-radioactive ELISA assay methods use specific phospho-antibodies (phospho-ABs), The phospho-AB binds only the phosphorylated substrate. This binding can be detected by chemiluminescence using a second peroxidase-conjugated anti-sheep antibody (Ross et al., Biochem. J. 366: 977-981, 2002).

There are many diseases and conditions associated with deregulation of cell proliferation and cell death (apoptosis). The diseases and conditions that can be treated, prevented or ameliorated by compounds according to the invention include, but are not limited to, the diseases and conditions listed below. The compounds according to the invention are suitable in the treatment and/or prophylaxis of a number of different diseases and conditions where there is proliferation and/or migration of smooth muscle cells and/or inflammatory cells into the intimal layer of a vessel, resulting in restricted blood flow through that vessel, for example in the case of neointimal occlusive lesions. Occlusive transplant vascular diseases of interest include atherosclerosis, coronary vascular disease after transplantation, vein graft stenosis, peri-anastomotic prosthetic restenosis, restenosis after angioplasty or stent placement and the like.

The present invention encompasses the use of the compounds according to the invention for the treatment or prevention of cancer. In particular, the invention relates to the use of compounds according to the invention and/or physiologically acceptable salts, derivatives, solvates and stereoisomers thereof, including mixtures thereof in all ratios, for the preparation of a medicament for the treatment and/or prophylaxis of solid tumours, where the solid tumour is particularly preferably selected from the group consisting of brain tumour, tumour of the urogenital tract, tumour of the lymphatic system, stomach tumour, laryngeal tumour, lung tumour. Solid tumours selected from the group consisting of monocytic leukaemia, lung adenocarcinoma, small-cell and non-small-cell lung carcinomas, renal cell carcinoma, endometrial carcinoma, multiple myeloma, prostate cancer, colorectal cancer, pancreatic cancer, glioblastomas and breast carcinoma can preferably also be treated with medicaments comprising compounds according to the invention.

The compounds according to the invention can be administered to patients for the treatment of cancer. By binding to IGF-1R, the present compounds inhibit tumour angiogenesis, thereby affecting the growth of tumours (S. E. Dunn et al. Mol Carcinog. January 2000;27(1):10-7). The properties of the compounds according to the invention make the latter also appear suitable for the treatment of certain forms of blindness related to retinal neovascularisation.

The invention therefore also relates to the use of compounds according to the invention and/or physiologically acceptable salts, derivatives, solvates and stereoisomers thereof, including mixtures thereof in all ratios, for the preparation of a medicament for the treatment and or prophylaxis of diseases that are caused, mediated and/or propagated by angiogenesis.

Such a disease in which angiogenesis is implicated is an ocular disease, such as retinal vascularisation, diabetic retinopathy, age-induced macular degeneration and the like.

The invention therefore also relates to the use of the compounds according to the invention for the preparation of a medicament for the treatment and/or prophylaxis of the above diseases.

The use of compounds according to the invention and/or physiologically acceptable salts and solvates thereof for the preparation of a medicament for the treatment and/or prophylaxis of inflammatory diseases also falls within the scope of the present invention. Examples of such inflammatory diseases include rheumatoid arthritis, psoriasis, contact dermatitis, delayed hypersensitivity reaction and the like.

Preference is given to the use for the treatment of diseases, preferably from the group of hyperproliferative and non-hyperproliferative diseases. These are cancerous diseases or non-cancerous diseases.

The invention also relates to the use of compounds according to the invention and/or physiologically acceptable salts, derivatives, solvates and stereoisomers thereof, including mixtures thereof in all ratios, for the preparation of a medicament for the treatment of diseases selected from the group of non-cancerous diseases consisting of psoriasis, arthritis, inflammation, endometriosis, scarring, benign prostatic hyperplasia, immunological diseases, autoimmune diseases and immunodeficiency diseases.

The invention furthermore relates to the use of compounds according to the invention and/or physiologically acceptable salts, derivatives, solvates and stereoisomers thereof, including mixtures thereof in all ratios, for the preparation of a medicament for the treatment of diseases selected from the group of cancerous diseases consisting of brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphoma, multiple myeloma, chronic leukaemia and acute leukaemia.

The present compounds are also suitable for combination with known anti-cancer agents. These known anti-cancer agents include the following: oestrogen receptor modulators, androgen receptor modulators, retinoid receptor modulators, cytotoxic substances, antiproliferative agents, prenylprotein transferase inhibitors, HMG-CoA reductase inhibitors, HIV protease inhibitors, reverse transcriptase inhibitors, growth factor inhibitors and angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethothoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenyl-retinamide.

"Cytotoxic substances" refers to compounds which result in cell death primarily through direct action on the cellular function or which inhibit or interfere with cell mitosis, including alkylating agents, tumour necrosis factors, intercalators, microtubulin inhibitors and topoisomerase inhibitors. Examples of cytotoxic substances include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)mu-[diamineplatinum(II)]bis[diamine(chloro)platinum(II)] tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H, 12H-benzo[de]pyrano[3,4';b,7]indolizino[1,2b]quinoline-10,13(9H, 15H)-dione, lurtotecan, 7-[2-(N-isopropylamino)ethyl]-(2OS)camptothecin, BNP 1350, BNPI1100, BN80915, BN80942, etoposide phosphate, teniposide; sobuzoxane, 2'-dimethylamino-2'-deoxyetoposide, GL331, N-[2-(dimethyl-amino)ethyl]-9-hydroxy-5,6-dimethyl-6H-pyrido[4,3-b]carbazole-1-carboxamide, asulacrine, (5a,5aB,8aa, 9b)-9-[2-[N-[2-(dimethylamino)ethyl]-N-methylamino] ethyl]-5-[4-hydroxy-3,5-dimethoxyphenyl]-5,5a,6,8,8a,9-hexo-hydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-amino-ethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]-acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-di-hydrobenzofuryl)sulfonyl]-N'-(3,4-dichlorophenyl)urea, N6-[4-deoxy-4-[N2-[2(E), 4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo-(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors, such as erbitux, trastuzumab, and tumour suppressor genes, such as p53, which can be delivered via recombinant virus-mediated gene transfer (see U.S. Pat. No. 6,069,134, for example).

WORKING EXAMPLES

Example 1

Preparation of (2-chloropyrimidin-4-yl)quinolin-3-ylamine 50 g (0.34 mol) of 2,4-dichloropyrimidine and 50 g (0.35 mol) of 3-amino-quinoline are combined and kept at the boil under reflux for 50 h in 400 ml of 2-propanol with 100 ml of ethyldiisopropylamine. The reaction mixture is poured into 3 l of ice-water, the precipitate is filtered off with suction and washed with water. The residue is recrystallised from acetone, giving 60 g of pale-grey crystals (m.p.: 140-143° C.) (2-chloropyrimidin-4-yl)quinolin-3-ylamine.

Example 2

Preparation of (4-aminophenyl)-(2,3-dihydro-1H-indol-7-yl)-methanone 5 g (42 mmol) of indoline are dissolved in 50 ml of toluene. In a separate flask, 70 ml of toluene are cooled to 5° C., and 100 ml of boron trichloride (10% solution in xylene) are added dropwise at this temperature under nitrogen. The indoline is subsequently added dropwise to this solution at 5-10° C., and 5.4 g (46 mmol) of 4-aminobenzonitrile are subsequently added in portions over the course of 30 min. The mixture is stirred at 5-10° for a further 15 min, and 6.7 g (50 mmol) of aluminium chloride are then added in portions at the temperature indicated. The mixture is heated under reflux for 6 h. For work-up, the reaction mixture is cooled to 70° C., and 10 ml of water are added dropwise, during which the temperature rises slightly and the solution becomes cloudy. 60 ml of 2 N hydrochloric acid are subsequently added, during which a clear solution is again formed, and the mixture is warmed under reflux for 12 h. The reaction mixture is poured into ice-water, adjusted to pH=12 using conc. NaOH and extracted with ethyl acetate. The combined organic phases are dried over sodium sulfate and evaporated, and the residue is chromatographed over a column with ethyl acetate. The combined product fractions are recrystallised from petroleum ether, giving 3.8 g of yellow crystals (4-aminophenyl)-(2,3-dihydro-1H-indol-7-yl)methanone. (M.p. 133-135° C.)

The following are likewise prepared by this protocol:
(4-benzyloxyphenyl)-(2,3-dihydro-1H-indol-7-yl)methanone
(2,3-dihydro-1H-indol-7-yl)-(4-hydroxyphenyl)methanone
(2,3-dihydro-1H-indol-7-yl)pyridin-4-ylmethanone
(2,3-dihydro-1H-indol-7-yl)pyridin-3-ylmethanone The ketones prepared by the process described above can be reduced to the corresponding alcohols at RT under atmospheric pressure using catalysts known to the person skilled in the art, such as, for example, Pd/C. Using platinum(IV) oxide, the pyridine is also reduced in addition to the ketone. Alternatively, the carbonyl group can be reduced selectively using reducing agents such as, for example, sodium borohydride. The following alcohol derivatives of the formula I can be obtained in this way:
(1H-indol-7-yl)piperidin-4-ylmethanol
(1H-indol-7-yl)pyridin-4-ylmethanol
(2,3-dihydro-1H-indol-7-yl)piperidin-4-ylmethanol
(2,3-dihydro-1H-indol-7-yl) pyridin-4-ylmethanol,
where the indoles are optionally prepared from the indolines by oxidation, for example using CrO3.

Example 3

Preparation of (2,3-dihydro-1H-indol-7-yl)-{4-[4-(quinolin-3yl-amino)pyrimidin-2-ylamino]phenyl}methanone 200 mg (0.84 mmol) of (4-aminophenyl)-(2,3-dihydro-1H-indol-7-yl)methanone and 215 mg (0.84 mmol) of (2-chloropyrimidin-4-yl)quinolin-3-ylamine are warmed at 120° C. for 2 h in 2 ml of DMSO. The organic phase is stirred with ethyl acetate and water and purified by chromatography over silica gel after phase separation, drying and evaporation, giving 500 mg of (2,3-di-hydro-1H-indol-7-yl)-{4-[4-(quinolin-3ylaminopyrimidin-2-ylamino]phenyl}-methanone. (M.p.: 235-238° C.)

The following is also prepared in this way:
(2,3-dihydro-1H-indol-7-yl)-{4-[2-(quinolin-3-ylamino)pyrimidin-4-ylamino]-phenyl}methanone.

Example 4

Inhibition of IGF-1R (IC$_{50}$)

Cultivated human tumour cells which express the IGF1 receptor (IGF1R) (for example MCF-7 or Calu-6) are stimulated using human IGF1, the natural ligand of IGF1R. The stimulation induces autophosphorylation of tyrosine residues in the cytoplasmatic IGF1R domain, which triggers signal transduction cascades, which result in apoptosis inhibition and cell proliferation.

The amount of phosphorylated IGF1R is determined by a receptor-specific Capture-ELISA or an analogous LUMINEX assay. The IGF1R from cell lysates is bound to a 96-well ELISA plate or LUMINEX beads ("capturing") by means of a specific antibody, and the tyrosine phosphorylation is detected using a biotin-labelled anti-phosphotyrosine antibody and a streptavidin peroxidase conjugate by a chemoluminescence method or by means of a fluorescence-labelled anti-phosphotyrosine antibody.

In order to determine the activity of kinase inhibitors, cells are pre-treated with increasing concentrations of these compounds for 45 min and subsequently stimulated using IGF1 for 5 min. As internal control, the biological activity of the ligand IGF1 is checked and a concentration series of an IGF1R reference inhibitor measured.

The following result is obtained in accordance with this procedure for (2,3-dihydro-1H-indol-7-yl)-{4-[4-(quinolin-3ylamino)pyrimidin-2-ylamino]-phenyl}methanone: the substance inhibits the kinase IGF-1R to the extent of 50% if the compound is present in a concentration of 120 nM.

Further inhibition constants of compounds according to the invention are shown in Table 1.

The following examples relate to pharmaceutical compositions:

Example 5a

Injection Vials

A solution of 100 g of an active ingredient according to the invention and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

Example 5b

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

Example 5c

Solution

A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example 5d

Ointment 500 my of an active ingredient according to the invention are mixed with 99.5 g of Vaseline under aseptic conditions.

Example 5e

Tablets

A mixture of 1 kg of active ingredient, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

Example 5f

Dragees

Tablets are pressed analogously to Example 5e and subsequently coated in a conventional manner with a coating of sucrose, potato starch, talc, tragacanth and dye.

Example 5g

Capsules 2 kg of active ingredient are introduced into hard gelatine capsules in a conventional manner in such a way that each capsule contains 20 mg of the active ingredient.

Example 5h

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:
1. A compound selected from the group consisting of
(2,3-dihydro-1H-indol-7-yl)-{4-[4-(quinolin-3-ylamino) pyrimidin-2-ylamino]phenyl}methanone,
[4-(2-chloropyrimidin-4-ylamino)phenyl]-(1H-indol-7-yl)methanone,
[4-(2-chloropyrimidin-4-ylamono)phenyl]-(2,3-dihydro-1H-indol-7-yl)-methanone,
(2,3-dihydro-1H-indol-7-yl)-(4-{4-[(pyridin-3-ylmethyl) amino]pyrimidin-2-ylamino}phenyl)methanone,
(1H-indol-7-yl)-{4-[2-(3,4,5-trimethoxyphenylamino)pyrimidin-4-ylamino]phenyl}methanone,
(4-{2-[4-(1H-indole-7-carbonyl)phenylamino]pyrimidin-4-ylamino}-phenyl)-(1H-indol-7-yl)methanone,
(4-{2-[4-(3-cyano-1H-indole-7-carbonyl)phenylamino] pyrimidin-4-ylamino}phenyl)-(3-cyano-1H-indol-7-yl) methanone,
3-{4-[4-(1H-indole-7-carbonyl)phenylamino]pyrimidin-2-ylamino}-propionitrile,
(4-{2-[(3-hydroxycyclobutylmethyl)amino]pyrimidin-4-ylamino}-phenyl)-(1H-indol-7-yl)methanone,
{4-[2-(1H-imidazol-2-ylamino)pyrimidin-4-ylamino] phenyl}-(1H-indol-7-yl)methanone,
(1H-indol-7-yl)-{3-[4-(quinolin-3-ylamino)pyrimidin-2-ylamino]-1H-pyrazol-4-yl}methanone,
(1H-indol-7-yl)-{4-[2-(5-phenyl-1H-pyrazol-3-ylamino) pyrimidin-4-ylamino]phenyl}methanone,
(1H-indol-7-yl)-{4-[2-(5-methyl-1H-pyrazol-3-ylamino) pyrimidin-4-ylamino]phenyl}methanone,
{4-[2-(5-furan-2-yl-1H-pyrazol-3-ylamino)pyrimidin-4-ylamino]-phenyl}-(1H-indol-7-yl)methanone,
{4-[2-(5-tert-butyl-1H-pyrazol-3-ylamino)pyrimidin-4-ylamino]-phenyl}-(1H-indol-7-yl)methanone,
(1H-indol-7-yl)-{4-[2-(1H-pyrazol-3-ylamino)pyrimidin-4-ylamino]-phenyl}methanone,
(2,3-dihyro-1H-indol-7-yl)-{4-[2-(quinolin-3-ylamino) pyrimidin-4-ylamino]phenyl}methanone, or a pharmaceutically acceptable salt stereoisomer, or mixture thereof.

2. A pharmaceutical composition comprising at least one compound according to claim 1 and/or physiologically acceptable salts stereoisomers, or mixtures thereof and a pharmaceutically acceptable carrier.

3. A pharmaceutical composition comprising at least one compound according to claim 1 and/or physiologically acceptable salts stereoisomers or mixtures thereof, and at least one further pharmaceutically active ingredient.

4. A kit consisting of separate packs of
a) an affective amount of a compound according to claim 1 and/or physiologically acceptable salts stereoisomers or mixtures thereof, and
b) an effective amount of a further medicament active ingredient.

* * * * *

UNITED STATES PATENT AND TRADEMARK OFFICE
CERTIFICATE OF CORRECTION

PATENT NO.        : 8,114,882 B2
APPLICATION NO.   : 11/911268
DATED             : February 14, 2012
INVENTOR(S)       : Heinrich et al.

It is certified that error appears in the above-identified patent and that said Letters Patent is hereby corrected as shown below:

Column 38, line 2 reads, "a) an affective amount of compound to claim 1," SHOULD READ
-- a) an effective amount of compound to claim 1, --

Signed and Sealed this
Twentieth Day of November, 2012

David J. Kappos
*Director of the United States Patent and Trademark Office*